United States Patent
Burgos et al.

(10) Patent No.: US 8,198,054 B2
(45) Date of Patent: Jun. 12, 2012

(54) METHOD FOR THE CHEMO-SELECTIVE ENZYMATIC HYDROLYSIS IF A DIESTER COMPOUND FOR PREPARING A MONOESTER MONOACID COMPOUND

(75) Inventors: Alain Burgos, Les Ponts de Ce (FR); Jean-Claude Caille, Angers (FR); Michelle Lorraine-Gradley, Kanterbury (GB)

(73) Assignees: Zach System, Avrille (FR); Novacta Biosystem Limited, Hertfordshire (GB)

( * ) Notice: Subject to any disclaimer, the term of this patent is extended or adjusted under 35 U.S.C. 154(b) by 326 days.

(21) Appl. No.: 12/523,602

(22) PCT Filed: Jan. 22, 2008

(86) PCT No.: PCT/FR2008/050095
§ 371 (c)(1),
(2), (4) Date: Nov. 20, 2009

(87) PCT Pub. No.: WO2008/110706
PCT Pub. Date: Sep. 18, 2008

(65) Prior Publication Data
US 2010/0068770 A1 Mar. 18, 2010

(30) Foreign Application Priority Data
Jan. 22, 2007 (FR) ...................... 07 52792

(51) Int. Cl.
*C12P 7/40* (2006.01)
(52) U.S. Cl. ........ 435/136; 435/195; 435/196; 435/197; 435/198
(58) Field of Classification Search ............... 435/136, 435/195, 196, 197, 198
See application file for complete search history.

(56) References Cited

U.S. PATENT DOCUMENTS
2004/0249188 A1  12/2004  Reddy et al. ............... 560/64

FOREIGN PATENT DOCUMENTS
JP  4-252189 A  9/1992
JP  6-228053 A  8/1994

OTHER PUBLICATIONS
Grell, W., et al. "Repaglinide and Related Hypoglycemic Benzoic Acid Derivatives", J. Med. Chem., vol. 41, 1998, pp. 5219-5246.

*Primary Examiner* — Susan Hanley
(74) *Attorney, Agent, or Firm* — Hamre, Schumann, Mueller & Larson, P.C.

(57) ABSTRACT

This disclosure relates to the synthesis of the compound of formula (I) according to Scheme A below:

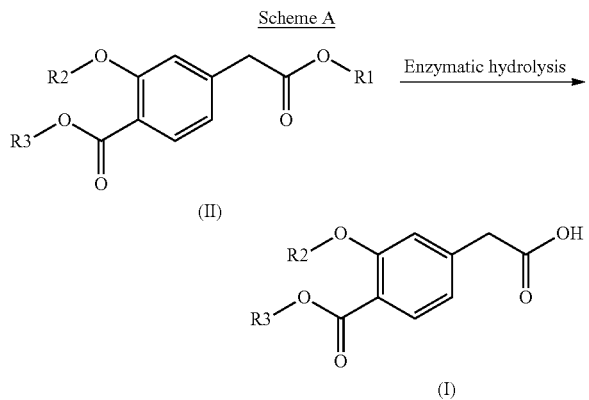

in which R1, R2 and R3, which may be identical or different, represent, individually and independently, an alkyl group, characterized by an enzymatic hydrolysis reaction that involves placing the compound of formula (II) in contact with an enzyme that performs a chemoselective hydrolysis of only one of the two ester functions of the compound of formula (II) to obtain the compound of formula (I).

24 Claims, No Drawings

METHOD FOR THE CHEMO-SELECTIVE ENZYMATIC HYDROLYSIS IF A DIESTER COMPOUND FOR PREPARING A MONOESTER MONOACID COMPOUND

INTRODUCTION

The present invention relates to a process for synthesizing a 4-carboxymethyl-2-alkyloxybenzoic acid, alkyl ester derivative from the diester derivative.

More specifically, it is a process for preparing 4-carboxymethyl-2-ethoxybenzoic acid, ethyl ester,

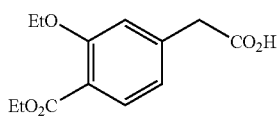

which is a key intermediate for the industrial production of the pharmaceutical active principle repaglinide, which is used in the treatment of diabetes.

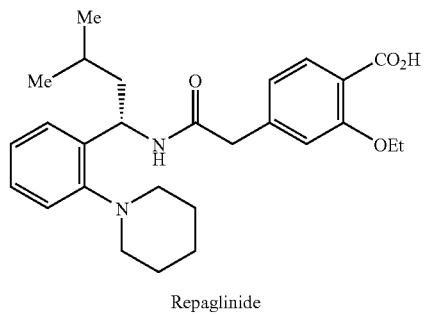

Repaglinide

PRIOR ART

The prior art discloses the article by the author P. Müller et al. published in the review J. Med. Chem., 1998, 41(26), p. 5219, describing a process for synthesizing 4-carboxymethyl-2-ethoxybenzoic acid, ethyl ester, characterized by a selective hydrolysis reaction of the corresponding diester derivative.

This selective hydrolysis reaction is performed in ethanol at a temperature of 25° C. and in the presence of a strong base, for instance an aqueous sodium hydroxide solution.

The limits of this process for an industrial use remain the formation of by-products in appreciable amount, especially the diacid compound that is difficult to remove, the need for several extraction and washing treatments or several recrystallizations to isolate the product and, finally, the low mass yield for production of the expected product.

Moreover, the prior art does not describe any process for preparing a phenylacetic acid compound comprising an ester function on the aromatic nucleus, using a chemoselective enzymatic hydrolysis reaction of a corresponding diester compound.

In particular, a process for the chemoselective enzymatic hydrolysis of an ester function of a phenylacetic acid relative to an ester function of a benzoic acid on a compound comprising these two functions is not described in the prior art.

AIMS OF THE INVENTION

A main aim of the present invention is to solve the novel technical problem that consists in providing a novel process for preparing 4-carboxymethyl-2-ethoxybenzoic acid, ethyl ester, while avoiding the formation of by-products and increasing the mass yield.

A main aim of the present invention is also to solve the novel technical problem that consists in providing such a novel process so as to minimize the production cost.

Another main aim of the present invention is to solve the novel problems stated above according to a novel process for preparing the said synthesis intermediate in amounts and quality that are industrially compatible with a pharmaceutical production.

SUMMARY OF THE INVENTION

The Applicant has now developed a novel process for synthesizing the compound of formula (I), as defined hereinbelow.

More particularly, this process is performed according to Scheme A below:

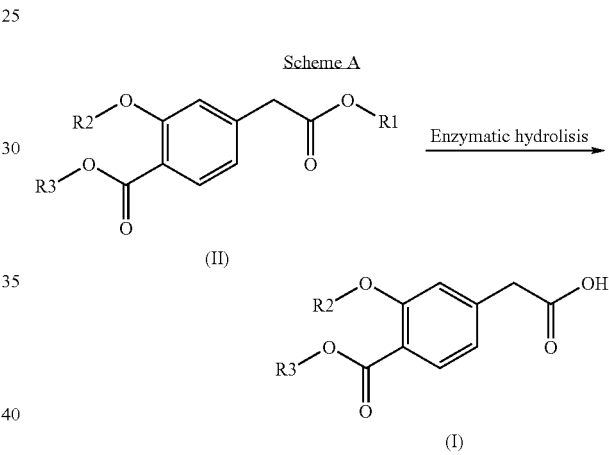

in which R1, R2 and R3, which may be identical or different, represent, individually and independently, an alkyl group.

According to one particular embodiment, each group R1, R2 and R3 is simultaneously identical, advantageously an ethyl.

In the context of the invention, the compound of formula (I) is obtained by performing a chemoselective enzymatic hydrolysis reaction of one of the two ester functions.

This process according to the invention is characterized by an enzymatic hydrolysis reaction that involves placing the compound of formula (II) in contact with an enzyme that performs a chemoselective hydrolysis of only one of the two ester functions of the compound of formula (II) to obtain the compound of formula (I). In the context of the invention, for the preparation of repaglinide, chemoselective hydrolysis of the ester function in position 4 of the intermediate is performed.

According to another advantageous embodiment of this process, the enzymatic hydrolysis reaction is performed in a solution at controlled pH in the presence or absence of an organic co-solvent. The pH value of the solution is controlled during the reaction so that the activity of the enzyme is not affected by this value, this value in particular being maintained between 6 and 8 during the reaction.

According to yet another advantageous embodiment of this process, for the preparation of the synthesis intermediate of repaglinide, the enzymatic hydrolysis reaction is performed at a controlled pH by using a buffer solution such as an aqueous solution based on phosphate, carbonate or sulfate with a pH value of between 6 and 8. More generally, the pH value of the buffer solution is such that it does not affect the activity of the enzyme used.

In particular, the buffer solution is an aqueous solution with a pH value equal to about 7.2.

According to one particular embodiment of the invention, this aqueous buffer solution may be obtained by using an aqueous solution based on phosphate, carbonate or sulfate, adjusted to an initial pH value of between 6 and 8. Such an aqueous buffer solution is commercially available.

According to one embodiment variant, an aqueous buffer solution with an initial pH of about 7.2, in particular based on potassium phosphate, is used.

According to another particular embodiment of the invention, the process is characterized in that control of maintenance of the pH value between 6 and 8 during the process is performed by adding an aqueous solution of a strong base such as an alkali metal hydroxide or alkoxide.

The normality of the solution of the strong base is such that it allows satisfactory regulation of the pH value, enabling maintenance of the activity of the enzyme.

According to one advantageous embodiment, in order to ensure maintenance of the activity of the enzyme and to avoid significant hydrolysis of the second ester function, in particular in position 1 in the context of manufacturing repaglinide, control of the pH value of the reaction medium is performed by adding a strong base such as an alkali metal hydroxide or alkoxide.

Preferentially, the pH control is performed by adding a sodium hydroxide solution, more particularly an aqueous sodium hydroxide solution. The normality of the basic solution is such that it allows satisfactory regulation of the pH value, enabling maintenance of the activity of the enzyme.

According to one advantageous embodiment of this process according to the invention, it is characterized in that the enzymatic hydrolysis reaction is performed at a temperature of between 10° C. and 70° C. and preferentially at a temperature of about 45° C.

According to another advantageous embodiment of the invention, the initial concentration of the starting material is between 1 kg/l and 50 g/l and preferentially between 500 g/l and 50 g/l, and the initial concentration is most preferentially about 400 g/l.

More generally, the initial concentration of the starting material is advantageously at the substantially maximum value that simultaneously affords solubility of the product in the selected solvent and no deterioration of the activity of the enzyme.

Among the enzymes used to perform this selective enzymatic hydrolysis, mention may be made of lipases, esterases, proteases, chirazymes and pancreatins.

The enzymes used may be in a solid form, in solution, in suspension or immobilized on an inert support.

The enzymes may be used directly either in the commercial form or after purification.

Non-limiting examples of enzymes that may be used in the context of the invention are chosen from a lipase, a lipase obtained from an *Aspergillus* (*Aspergilus niger*, *Aspergillus melleus*, *Aspergillus usuamii*), from a *Rhizopus* (*Rhizopus oryzae*, *Rhizopus niveus*, *Rhizopus* sp., *Rhizopus javenicus*, *Rhizopus delegar*, *Rhizopus delemar*), from a *Penicillium* (*Penicillium roquefortii*, *Penicillium camembertii*, *Penicillium cyclopium*), from a *Mucor* (lyophilized or supported *Mucor miehei* (chirazyme L9), *Mucor javanicus*, *Mucor javenicus*), from a *Candida* (*Candida antarctica*, lyophilized or supported *Candida antarctica* type A (chirazyme L5), lyophilized or supported *Candida antarctica* type B (chirazyme L2), *Candida cylindraceae*, *Candida lipolytica*, *Candida rugosa*), from a *Pseudomonas* (*Pseudomonas fluorescens*, *Pseudomonas cepacia*, *Pseudomonas aeruginosa*, *Pseudomonas stutzeri*, *Pseudomonas* species), from an Alkaligenes (*Alcaligenes* sp.), from a *Humicola* (*Humicola lanuginosa*, *Humicola* sp. Lipase), from a *Geotrichum* (*Geotrichum candidum*), from a pancreas (hog pancreas, pig pancreas), from an *Achromobacter* (*Achromobacter* sp.), from a *Thermomyces* (*Thermomyces lanuginosus*) and from a *Burkholderia* (*Burkholderia cepacia*).

Among the other lipases, mention may also be made, as a non-limiting guide, of a Lipase F14, a Lipase F10, a Lipase F12, a Lipase A1, a Lipase F7, a Lipase F13, a Lipase F8, a Lipase F2, a Lipase F3, an Amano 6, a Lipase AP15, a Lipase F, an Amano 50, a Lipase G, a Lipase F4, a Lipase F6, a Lipase B1, a Lipase PS-D1, a Lipase PS-C2, a Lipase 1, a Lipase 1, a Lipase 2, a Euroform Lipase 4, a Lipase 4, a Lipase 6, a Lipase 7, a Lipase 10, a Lipase 11, a Lipase 12, a Lipase 13, a Lipase 14, a Lipase 15, a Lipase 18, a Lipase 20, a Lipase PGE, an Ap-6 and a Lipolase.

As non-limiting examples, it is also possible to use in the context of the invention an enzyme chosen from an esterase, a pig liver esterase (PLE), ferulic acid esterase, paroxetine esterase and *Candida rugosa* esterase.

As non-limiting examples, it is also possible to use in the context of the invention an enzyme chosen from a protease, an enzyme obtained from a mixture of *Streptomyces* (*Streptomyces griseus*, *Streptomyces* serine), of *Subtilisin* (*Subtilisin carlsberg*), of a *Bacillus* (*Bacillus* sp., *Bacillus lantus*, *Bacillus stearothermophilus*) and of a *Carica* (*Carica papaya*).

As non-limiting examples, according to another embodiment variant, it is also possible to use an enzyme chosen from a chirazyme, Chirazyme L-8, Chirazyme L-2, Chirazyme L-2, Chirazyme L-5, Chirazyme L-10 and Chirazyme E1.

As non-limiting examples, according to another embodiment variant, it is also possible to use an enzyme chosen from another enzyme, Deamizyme 50000, Pancreatin, Depol (Depol 222P, Depol 454P, Depol 39, Depol 112L, Depol 40L, Depol 165L, Depol 239P, Depol 260P, Depol 333P, Depol 276P, Depol 39P), Promod (Promod 215P, Promod 31L, Promod 192P, Promod 144P, Promod 194P), Combizyme (Combizyme 261P, Combizyme 274P, Combizyme 108, Combizyme 23, Combizyme 209), Flavopro (Flavorpro 192P, Flavorpro 373P, Flavorpro 373P(X)), Macer8 (Macer8 O, Macer8 R, Macer8 W, Macer8 FJ), Pectinase (Pectinase 62L, Pectinase 444L), Lipomod 29P, Peptidase 433P, Lipoxygenase L583P, Cellulase 13L, Aminoacylase, Laccase L603P, Lactase L017P, Hemicellulase 344P, TP599P, SP398, Viscozyme L, Shearzyme 500L, Ultrazyme AFP-L, Peelzyme 1, Ultraflo L, Ultraflo L C809, SP525, Resinase A and Validase TR.

These enzymes are commercially available from companies such as Sigma, Amano, Europa, Biocatalysts, Boehringer, Novo-Nordisk, Biotal, Enzymatix, Fluka, Genecore, Novozymes. etc.

As non-limiting examples, according to another embodiment variant, it is also possible to use a commercial enzyme tested in the process of the invention, immobilized *Candida cylindracea* (Sigma), immobilized *Candida antarctica* B or Novozyme 435 (Novozymes), immobilized *Mucor miehei* (Fluka), immobilized *Pseudomonas cepacia* or PSD1 (Amano), *Pseudomonas menodicina* or Lumafast (Genecore), *Humicola lariuginosa* or Lipolase, *Aspergillus niger* or AP6 (Amano), *Penicillium camembertii* or Lipse G (Amano), Wheat germ (Fluka) or *Rhizopus niveus*.

Preferentially, the chosen enzyme is a lipase such as, in particular, an enzyme obtained from *Candida antarctica* type B, for example Novozyme 435 commercially available from the company Novozymes.

According to another embodiment of the invention, the ratio of the amount of enzyme used to the amount of substrate as a weight/weight value (the E/S ratio) is between 1/10 000 and 20/100 and preferentially between 1/1000 and 5/100.

According to yet another embodiment of the invention, the enzyme concentration may be between 0.001 g/l and 100 g/l and preferentially between 1 g/l and 10 g/l.

According to one particular embodiment variant, the incubation time of the enzyme is between 10 minutes and 4 days and is preferentially between 0.5 and 24 hours.

According to yet another particular embodiment variant, the organic co-solvent optionally used, alone or as a mixture, may be, as non-limiting examples, a sulfoxide such as dimethyl sulfoxide (DMSO), a nitrile such as acetonitrile, an alcohol such as ethanol, tert-butanol or isopropanol (IPA), an amide such as dimethylformamide (DMF), an ether such as ethyl ether, a hydrocarbon such as hexane, or an aromatic such as toluene.

The concentration of the co-solvent may be between 0.1% and 30%.

Once removed during the reaction work-up, the enzyme may be reused in the process of the invention.

More generally, the number of cycles of use of the enzyme may be between 1 and 5 and preferentially between 1 and 3.

DEFINITIONS

The definitions below are applicable to the description and to the claims of the invention.

To aid understanding, the nomenclature of the groups, reagents, solvents or products is the international nomenclature or the nomenclature commonly used by a person skilled in the art.

The term "alkyl" means a linear or branched alkyl chain formed from 1 to 10 carbon atoms.

The term "alkoxide" means a linear or branched alkyloxy group formed from 1 to 10 carbon atoms.

The term "alkali metal" means a sodium or potassium atom.

Other aims, characteristics and advantages of the invention will emerge clearly in the light of the explanatory description that follows, made with reference to several implementation examples of the invention, which are given purely as illustrations and shall not in any way limit the scope of the invention.

In the examples, the percentages are given on a weight basis, the temperature is in degrees Celsius and the pressure is atmospheric pressure, unless otherwise indicated.

To aid understanding, the nomenclature of the products used is the international nomenclature and the nomenclature of the reagents or solvents is that commonly used by a person skilled in the art.

EXAMPLE 1 OF THE INVENTION

Preparation of 4-carboxymethyl-2-ethoxybenzoic Acid, Ethyl Ester

Compound of formula (I) in which R is an ethyl group.
Lipase enzyme: Novozyme 435.
Buffer solution: aqueous 0.2 M potassium phosphate solution of pH 7.2.
The amount of enzyme used is 10 mg.
The reaction is performed in a hermetically sealed 4 ml glass flask, on a size of 1 ml.
The reaction volume is set at 1 ml by adapting the volume of buffer solution relative to the amount of starting material used.
The reaction is performed at 45° C.

EXAMPLE 1 A 50 mg of Diester (Concentration 50 g/l)

After reaction for 1 hour 50 minutes, a 100% degree of conversion is obtained.

EXAMPLE 1 B 100 mg of Diester (Concentration 100 g/l)

After reaction for 2 hours 50 minutes, a 100% degree of conversion is obtained.

EXAMPLE 1 C 200 mg of Diester (Concentration 200 g/l)

After reaction for 3 hours 50 minutes, an 80% degree of conversion is obtained.

EXAMPLE 2 OF THE INVENTION

Preparation of 4-carboxymethyl-2-ethoxybenzoic Acid, Ethyl Ester

Compound of formula (I) in which R is an ethyl group.
Enzyme: Novozyme 435.
Buffer solution: aqueous 0.1 M potassium phosphate solution of pH 7.2.
pH control: aqueous 2.5 M NaOH solution.
The reaction is performed in a hermetically sealed 100 ml glass flask. 3.86 g (13.8 mmol) of diester in a volume of 10 ml of phosphate buffer and 0.2 g of enzyme are added.
The medium is heated to a temperature of 45° C.
The pH value is maintained at 7.2 by regular addition of a sodium hydroxide solution.
After reaction for 1 hour 35 minutes, the degree of conversion is 100%.
The enzyme is removed from the medium by filtration. The cake is washed with warm water. The filtrates are combined and acidified with 20% hydrochloric acid (HCl) solution until a pH value of 3.5 is obtained.
The medium is stirred and then cooled in an ice bath for 1 hour. The precipitate formed is filtered off and then dried at a temperature of 45° C. to constant weight.
The product obtained is a white solid.
Yield: quantitative.
Purity: 99.3%

The invention comprises all the means constituting technical equivalents of the means described and also various combinations thereof. Any technical characteristic that appears to be novel relative to any PRIOR ART from the preceding description, including the examples, forms an integral part of the invention in its function and as a general means.

The invention claimed is:

1. A process for synthesizing a compound of formula (I) from a compound of formula (II), according to Scheme A below:

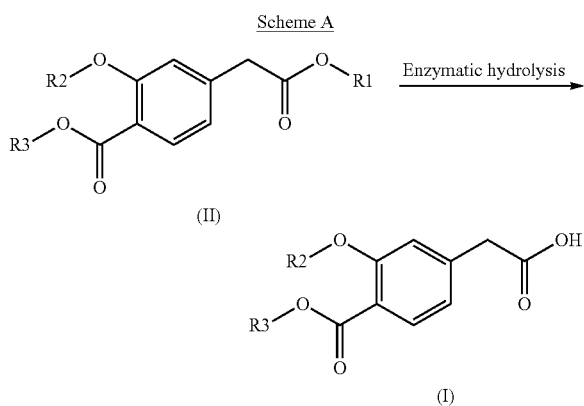

in which R1, R2 and R3, which may be identical or different, represent, individually and independently, an alkyl group, comprising placing the compound of formula (II) in contact with an enzyme selected from a lipase, an esterase, a chirazyme and a pancreatin, wherein the enzyme is present in a form selected from a solution, a suspension, and an immobilized form on an inert support, thereby chemoselectively hydrolysing the compound of formula (II).

2. The process of claim 1, wherein the hydrolysis is performed in a solution at a controlled pH.

3. The process of claim 2, wherein the pH is controlled by adding a buffer solution.

4. The process of claim 3, wherein the buffer solution is an aqueous solution formed from at least one of phosphate, carbonate and sulphate, with a pH value of between 6 and 8.

5. The process of claim 3, wherein the buffer solution is an aqueous solution comprises potassium phosphate with a pH value of between 6 and 8.

6. The process of claim 3, wherein the buffer solution has an initial pH value of about 7.2.

7. The process of claim 3, wherein the buffer solution is an aqueous solution formed from at least one of phosphate, carbonate and sulphate, with a pH value of between 6 and 8, and wherein the reaction temperature is about 45° C.

8. The process of claim 2, wherein the pH value is maintained between 6 and 8 during the reaction.

9. The process of claim 2, wherein the pH is controlled by adding an aqueous solution of a strong base.

10. The process of claim 9, wherein the strong base comprises sodium hydroxide.

11. The process of claim 2, wherein the pH is controlled by adding an aqueous solution of an alkali metal hydroxide or alkoxide.

12. The process of claim 1, wherein the hydrolysis is performed in the presence of an organic co-solvent.

13. The process of claim 1, wherein the enzyme comprises the lipase.

14. The process of claim 1, wherein the enzyme is used in a commercial form.

15. The process of claim 1, wherein the weight ratio of the amount of enzyme to the amount of substrate is between 1/10 000 and 20/100.

16. The process of claim 1, wherein the weight ratio of the amount of enzyme to the amount of substrate is between 1/1000 and 5/100.

17. The process of claim 1, wherein the initial concentration of the compound of formula II is between 1 kg/l and 50 g/l.

18. The process of claim 1, wherein the hydrolysis is performed at a temperature between 10° C. and 70° C.

19. The process of claim 1, wherein the hydrolysis is performed in the absence of an organic co-solvent.

20. The process of claim 1, wherein each group R1, R2 and R3 is simultaneously an ethyl.

21. The process of claim 1, wherein the enzyme is a lipase obtained from *Candida antarctica* type B.

22. The process of claim 1, wherein the initial concentration of the compound of formula (II) is about 400 g/l.

23. The process of claim 1, wherein the amount of enzyme is between 1 g/l and 10 g/l.

24. In a process of producing repaglinide, the improvement comprising preparing the intermediate of formula (I) by the process of claim 1.

* * * * *